United States Patent [19]
Simpson et al.

[11] Patent Number: 6,143,152
[45] Date of Patent: Nov. 7, 2000

[54] MICROFABRICATED CAPILLARY ARRAY ELECTROPHORESIS DEVICE AND METHOD

[75] Inventors: Peter C. Simpson, Oakland; Richard A. Mathies, Moraga, both of Calif.; Adam T. Woolley, Belmont, Mass.

[73] Assignee: The Regents of The University of California, Berkeley, Calif.

[21] Appl. No.: 08/965,738

[22] Filed: Nov. 7, 1997

[51] Int. Cl.[7] .......................... G01N 27/26; G01N 27/447
[52] U.S. Cl. .......................... 204/451; 204/453; 204/601; 204/604
[58] Field of Search .................... 204/451–453, 204/455, 601, 603–605; 435/287, 2, 6; 422/68.1, 100, 101, 102

[56] References Cited

U.S. PATENT DOCUMENTS

| | | | |
|---|---|---|---|
| 5,325,889 | 7/1994 | Paul et al. | 137/594 |
| 5,585,069 | 12/1996 | Zanzucchi et al. | 422/100 |
| 5,599,432 | 2/1997 | Manz et al. | 204/451 |
| 5,605,662 | 2/1997 | Heller et al. | 422/68.1 |
| 5,750,015 | 5/1998 | Soane et al. | 204/451 |
| 5,757,482 | 5/1998 | Fuchs et al. | 256/246 |
| 5,800,690 | 9/1998 | Chow et al. | 204/451 |
| 5,858,195 | 1/1999 | Ramsey . | |
| 5,976,336 | 11/1999 | Dubrow et al. . | |
| 6,001,229 | 12/1999 | Ramsey . | |
| 6,001,231 | 12/1999 | Kopf-Sill . | |
| 6,010,607 | 1/2000 | Ramsey . | |
| 6,010,608 | 1/2000 | Ramsey . | |
| 6,033,546 | 3/2000 | Ramsey . | |

FOREIGN PATENT DOCUMENTS

| | | |
|---|---|---|
| 0 665 430 | 8/1995 | European Pat. Off. . |
| WO 96 04547 | 2/1996 | WIPO . |
| WO 96 35810 | 11/1996 | WIPO . |
| WO 96 42013 | 12/1996 | WIPO . |
| WO 98/52691 | 11/1998 | WIPO . |

OTHER PUBLICATIONS

Burggraf et al. Synchronized Cyclic Capillary Electrophoresis: . . . Analytical Methods and Instrumentation. vol. 1, No. 1 (1993), pp. 55–59.

C. Alexay et al., "Fluorescence scanner employing a Macro Scanning Objective," *SPIE* vol. 2705, Apr. 1996, pp. 63–72.

Bartosiewicz et al., "Implementation of a capillary array electrophoresis instrument," *ISC Technical Publications, Inc.* Feb. 1996, pp. 61–68.

Chee et al., "Accessing Genetic Information with High–Density DNA Arrays," *Science* vol. 274, Oct. 25, 1996, pp. 610–614.

Clark et al., High–Speed Parallel Separation of DNA Restriction Fragments Using Capillary Array Electrophoresis, *Anal. Biochemistry 215*, 1993, pp. 163–170.

Clark et al., "Multiplex dsDNA Fragment Sizing Using Dimeric Intercalation Dyes and Capillary Array Electrophoresis:Ionic Effects on the Stability and Electrophoretic Mobility of DNA–Dye Complexes," *Analytical Chemistry*, vol. 69, No. 7, pp. 1355–1363, Apr. 1, 1997.

(List continued on next page.)

*Primary Examiner*—William H. Beisner
*Attorney, Agent, or Firm*—Townsend and Townsend and Crew LLP

[57] ABSTRACT

A capillary array electrophoresis (CAE) micro-plate with an array of separation channels connected to an array of sample reservoirs on the plate. The sample reservoirs are organized into one or more sample injectors. One or more waste reservoirs are provided to collect wastes from reservoirs in each of the sample injectors. Additionally, a cathode reservoir is also multiplexed with one or more separation channels. To complete the electrical path, an anode reservoir which is common to some or all separation channels is also provided on the micro-plate. Moreover, the channel layout keeps the distance from the anode to each of the cathodes approximately constant.

41 Claims, 11 Drawing Sheets

OTHER PUBLICATIONS

Cohen et al., "Separation and analysis of DNA sequence reaction products by capillary gel electrophoresis," *Journal of Chromatography*, 516, 1990, pp. 49–60.

Drossman et al., "High–Speed Separations of DNA Sequencing Reactions by Capillary Electrophoresis," *Anal. Chem.* vol. 62, 1990, pp. 900–903.

Effenhauser et al., "Glass Chips for High–Speed Capillary Electrophoresis Separations with Submicrometer Plate Heights," *Anal. Chem.*, vol. 65, 1993, pp. 2637–2642.

Effenhauser et al., "High–Speed Separation of Antisense Oligonucleotides on a Micromachined Capillary Electrophoresis Device," *Anal. Chem.* vol. 66, 1994, pp. 2949–2953.

Feder et al., "A novel MHC class I–like gene is mutated in patients with hereditary haemochromatosis," *Nature genetics*, vol. 13, Aug. 1996, pp. 399–408.

Glazer et al., "Energy–transfer fluorescent reagents for DNA analyses," *Anal. Biotech.*, 1997, pp. 94–102.

Harrison et al., "Capillary Electrophoresis and Sample Injection Systems Integrated on a Planar Glass Chip," *Anal. Chem.*, vol. 64, 1992, pp. 1926–1932.

Harrison et al., "Micromachining a Miniaturized Capillary Electrophoresis–Based Chemical Analysis System on a Chip," *Science*, vol. 261, Aug. 13, 1993, pp. 895–897.

S. Hjerten, "Elimination of Electroendosmosis and Solute Adsorption," *Journal of chromatography*, 347, 1985, pp. 191–198.

Huang et al., "Capillary Array Electrophoresis Using Laser–Excited Confocal Fluorescence Detection," *Anal. Chem.* vol. 64, 1992, pp. 968–972.

Huang et al., "DNA Sequencing Using Capillary Array Electrophoresis," *Anal. Chem.*, vol. 64, 1992, pp. 2149–2154.

Jacobson et al., "Microchip Capillary Elelctrophoresis with an Integrated Postcolumn Reactor," *Anal.Chem.*, vol. 66, 1994, pp. 3472–3476.

Jacobson et al., "Integrated Microdevice for DNA Restriction Fragment Analysis," *Anal.Chem.*, vol. 68, 1996, pp. 720–723.

Kleterpal et al., "DNA sequencing using a four–color confocal fluorescence capillary array scanner," *Electrophoresis*, vol. 17, 1996, pp. 1852–1859.

Kostichka et al., "High speed automated DNA sequencing in ultrathin slab gels." *Biotechnology*, vol. 10, Jan. 1992, pp. 78–81.

Landers et al., "Capillary Electrophoresis: A Powerful Microanlaytical Technique for Biologically Active Molecules," *Biotechniques*, vol. 14, No. 1, 1993, pp. 98–111.

Li et al., "Transport, Manipulation, and Reaction of Biological Cells On–Chip Using Electrokinetic Effects," *Anal. Chem.*, vol. 69, 1997, pp. 1564–1568.

Manz et al., " Capillary electrophoresis on a chip," *Journal of Chromatography*, 593, 1992, pp. 253–258.

Merryweather et al., "Global prevalence of putative haemochromatosis mutations," *Med Genet*, 1997, pp. 275–278.

Miller et al., "A simple salting out procedure for extracting DNA from human nucleated cells," *Nucleic Acids Research*, vol. 16, No. 3, 1988, p. 1215.

Scriver, M.D. et al., "The metabolic and molecular bases of inherited disease," Chemochromatosis, chapter 69, 1995, pp. 2237–2268.

G.F. Sensabaugh, "Commentary," *Blood Cells, Molecules, and Diseases*, 22, Aug. 31, 1996, pp. 194a–194b.

Simpson et al., "Microfabrication Technology for the Production of Capillary Array Electrophoresis Chips," Department of Chemistry, University of CA, Berkeley, pp. 15. No Date Provided.

Simpson et al., "High–throughput genetic analysis using microfabricated 96–sample capillary array electrophoresis microplates," *Proc. Natl. Acad. Sci. USA*, vol. 95, pp. 2256–2261, Mar. 1998, pp. 2256–2261.

Swerdlow et al., "Capillary gel electrophoresis for rapid, high resolution DNA sequencing," *Nucleic Acids Research*, vol. 18, No. 6, 1990 Oxford University Press, pp. 1415–1419.

Takahashi et al., "Multiple Sheath–Flow Gel Capillary–Array Electrophoresis for Multicolor Fluorescent DNA Detection," *Anal. Chem.* 1994, 66, pp. 1021–1026.

Ueno et al., "Simultaneous Monitoring of DNA Fragments Separated by Electrophoresis in a Multiplexed Array of 100 Capillaries," *Anal. Chem. 66*, 1994, pp. 1424–1431.

Wang et al., "High–resolution capillary array elelctrophoretic sizing of multiplexed short tandem repeat loci using energy–transfer fluorescent primers," *Electrophoresis*, 17, 1996, pp. 1485–1490.

Wang et al., "Microsatellite–based cancer detection using capillary array elelctrophoresis and energy–transfer fluorescent primers," *Electrophoresis*, 18, 1997, pp. 1742–1749.

Woolley et al., "Ultra–high–speed DNA fragment separations using microfabricated capillary array electrophoresis chips," *Proc. Natl. Acad. Sci. USA*, vol. 91, Nov. 1994, pp. 11348–11352.

Wolley et al., "Ultra–high–speed DNA sequencing using capillary electrophoresis chips," *Anal. Chem.*, 67, 1995, pp. 3676–3680.

Wolley et al., "Functional Integration of PCR Amplification and Capillary Electrophoresis in a Microfabricated DNA Analysis Device," *Anal. Chem.*, vol. 68, No. 23, pp. 4081–4086. (Dec. 1996).

Wolley et al., "High–speed DNA genotyping using microfabricated capillary array electrophoresis chips," *Anal. Chem.*, vol. 69, No. 11, pp. 2181–2186. (Jun. 1997).

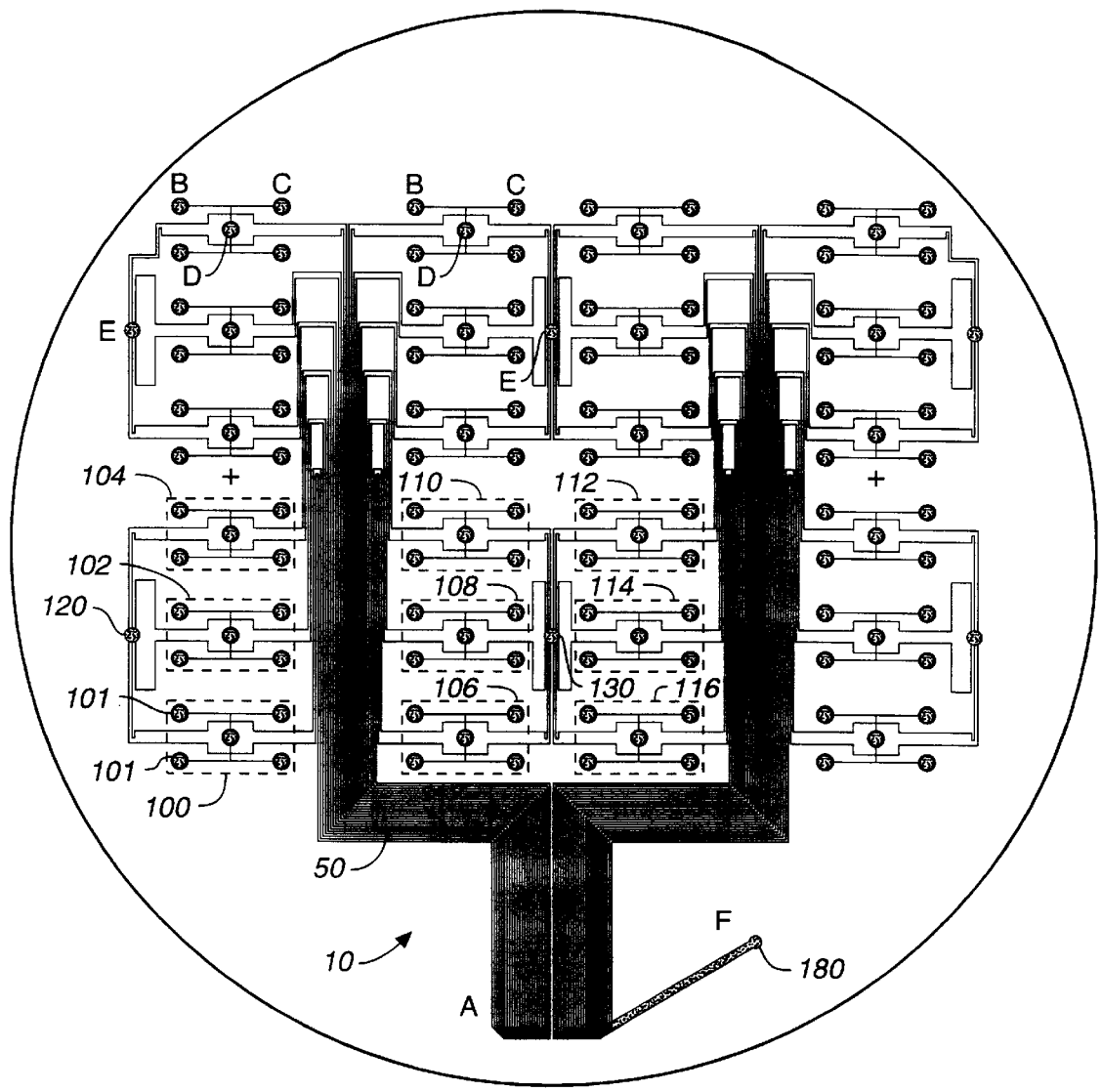
FIG._1

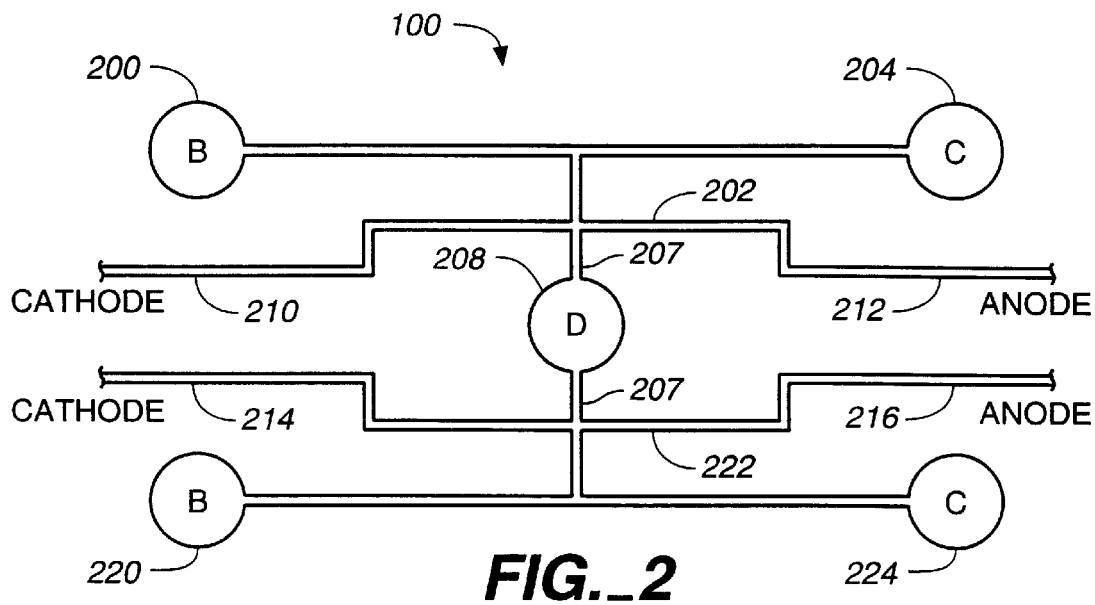
FIG._2
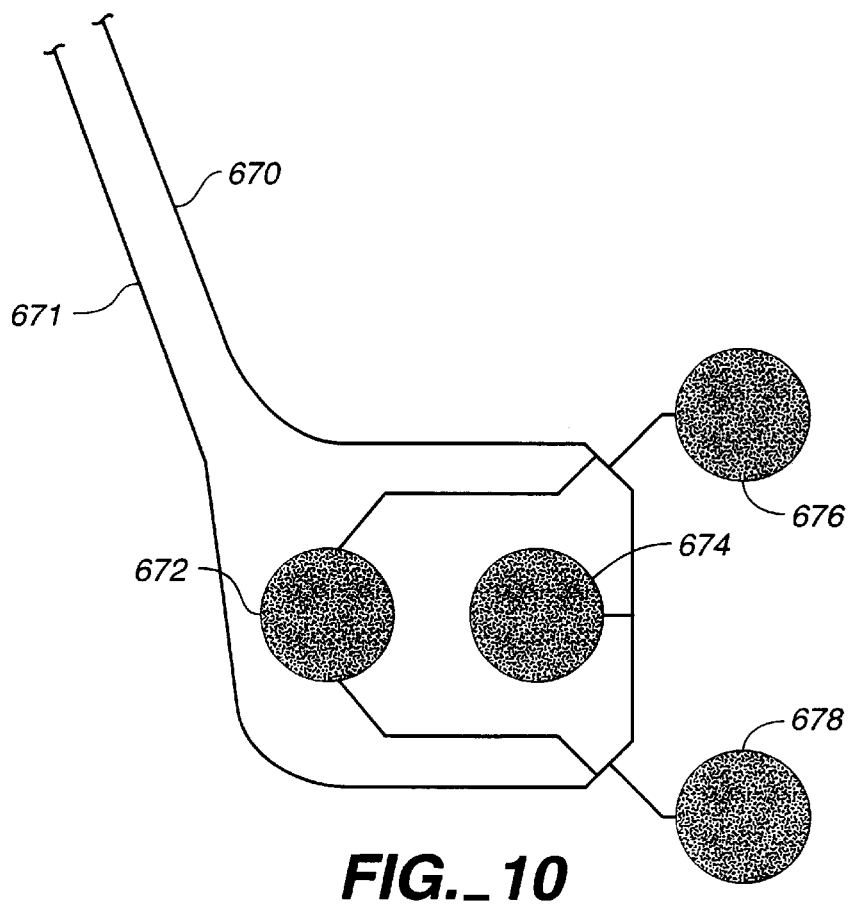
FIG._10

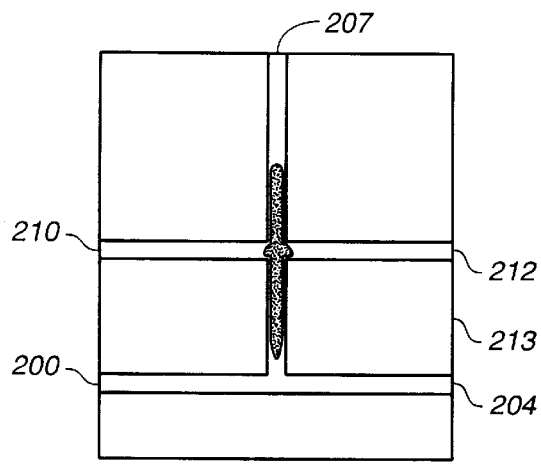
FIG._3A
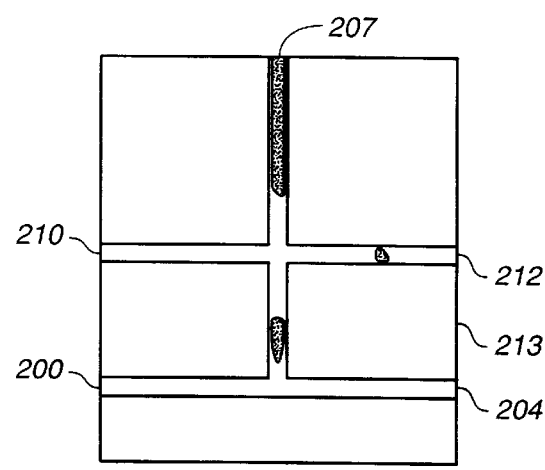
FIG._3B
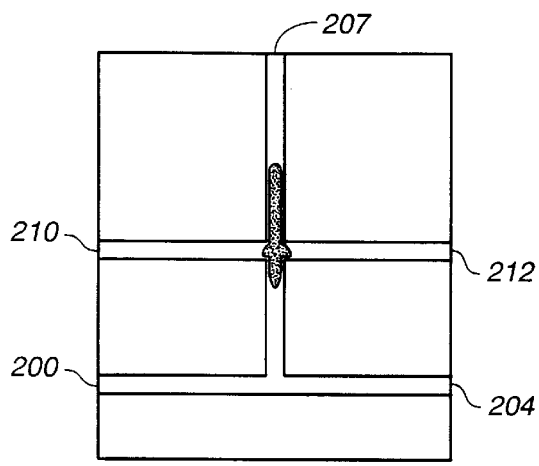
FIG._3C
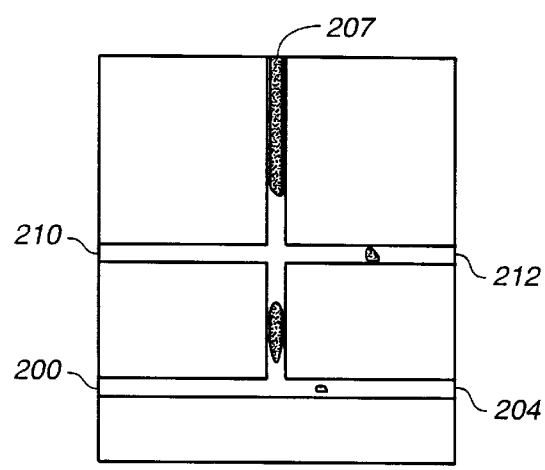
FIG._3D

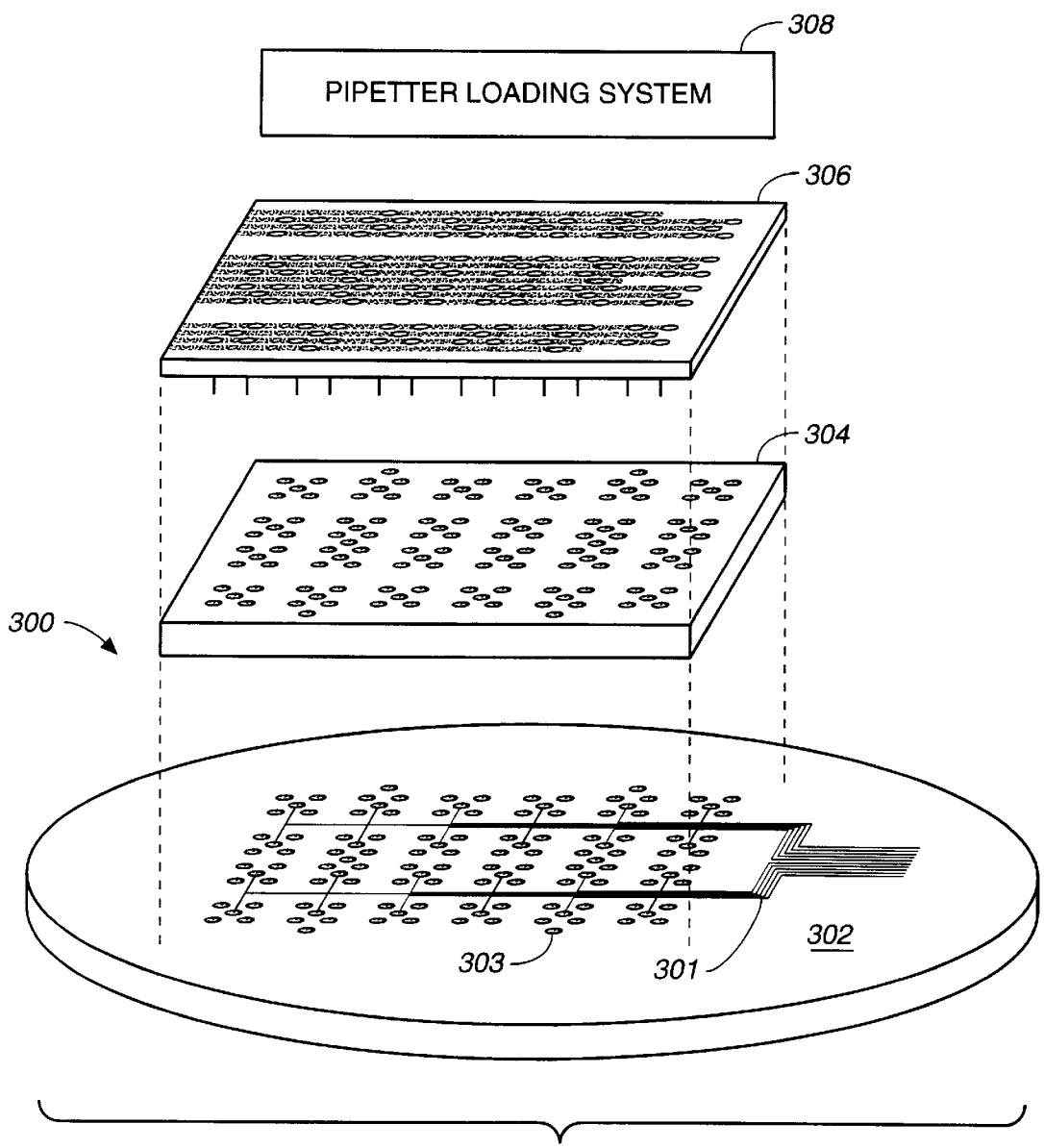
FIG._4A
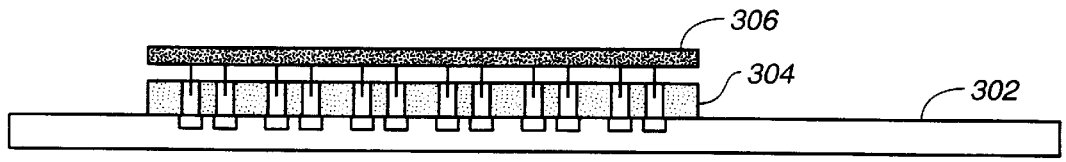
FIG._4B

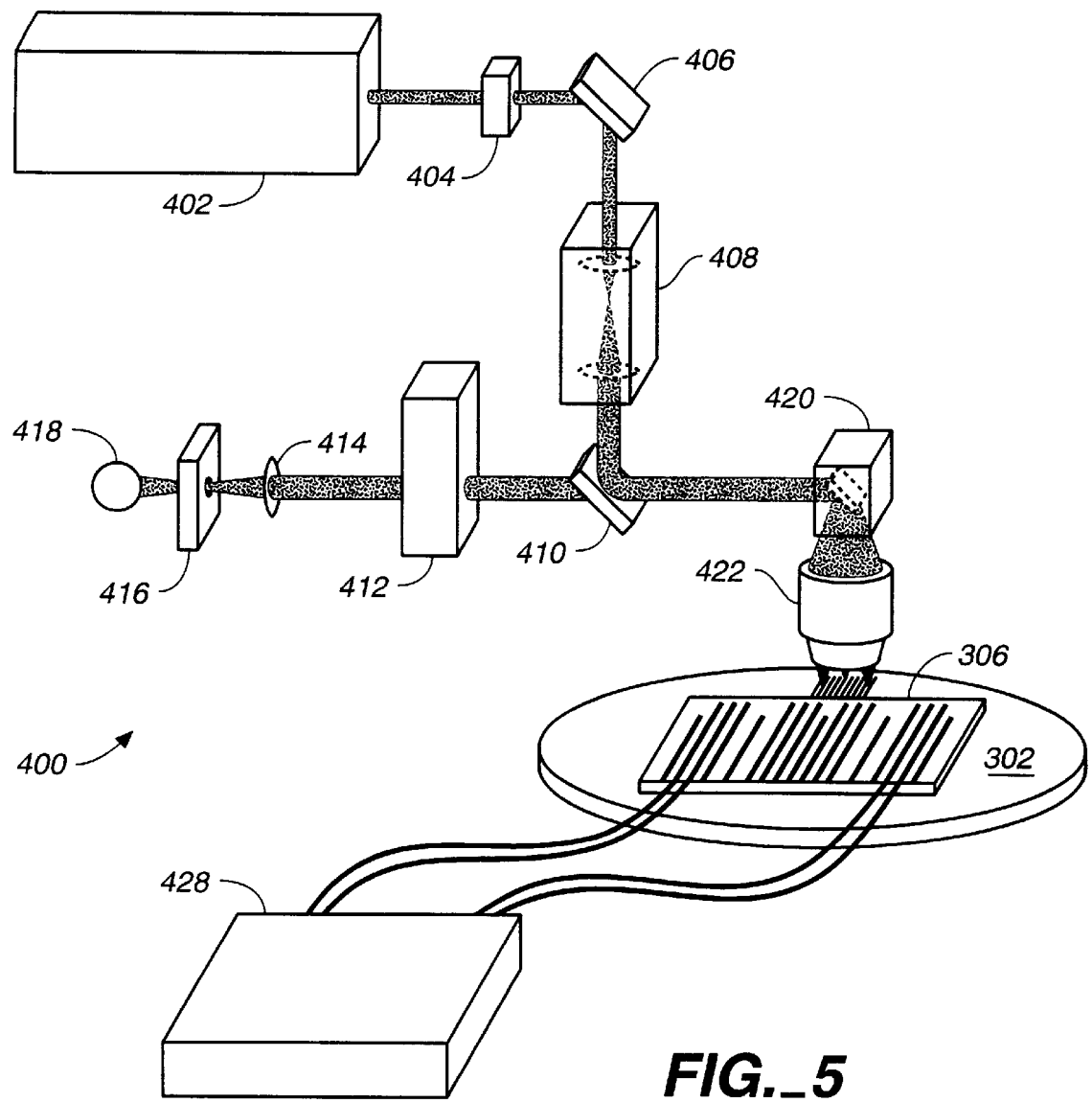
FIG._5

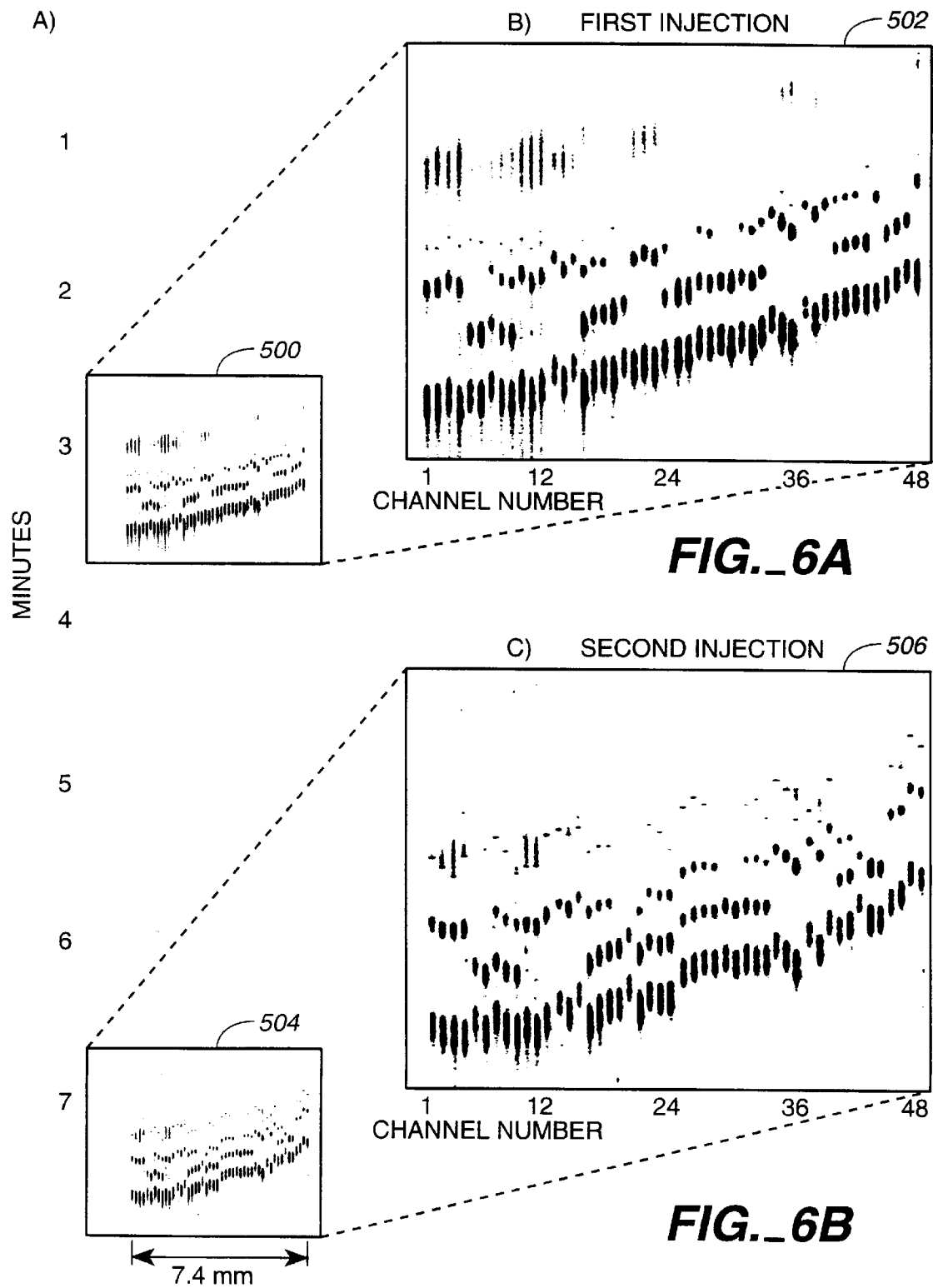
FIG._6A
FIG._6B

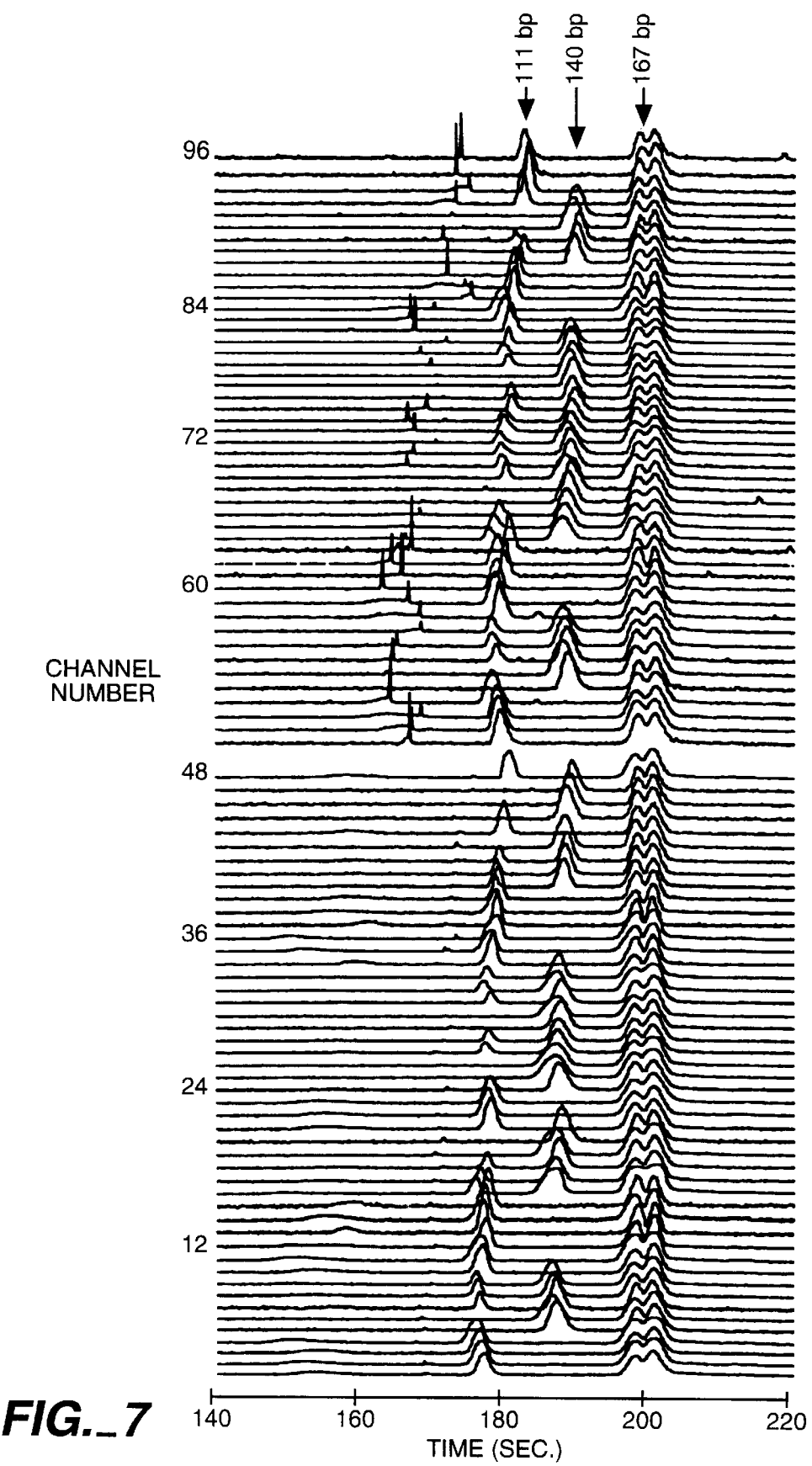
FIG._7

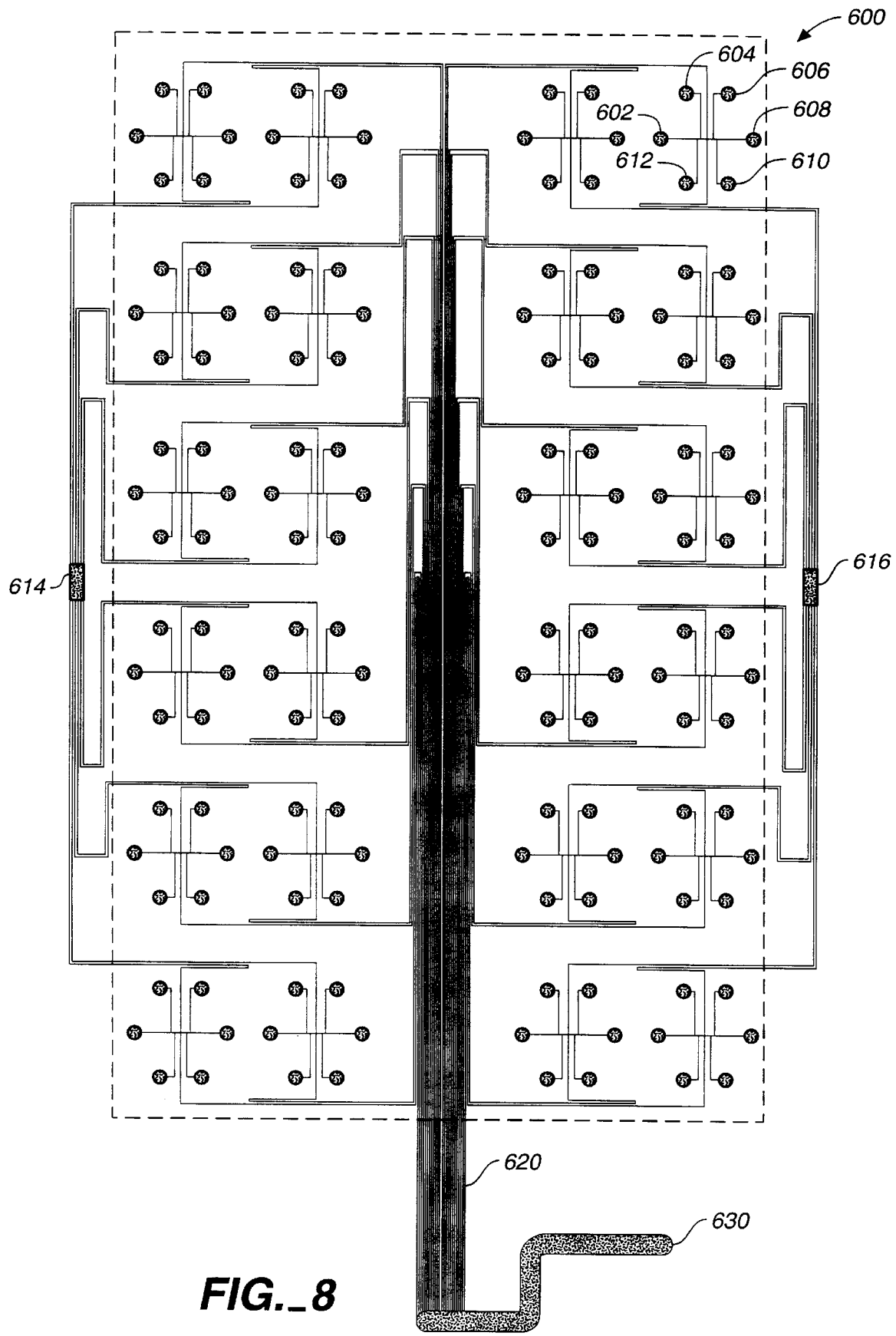
FIG._8

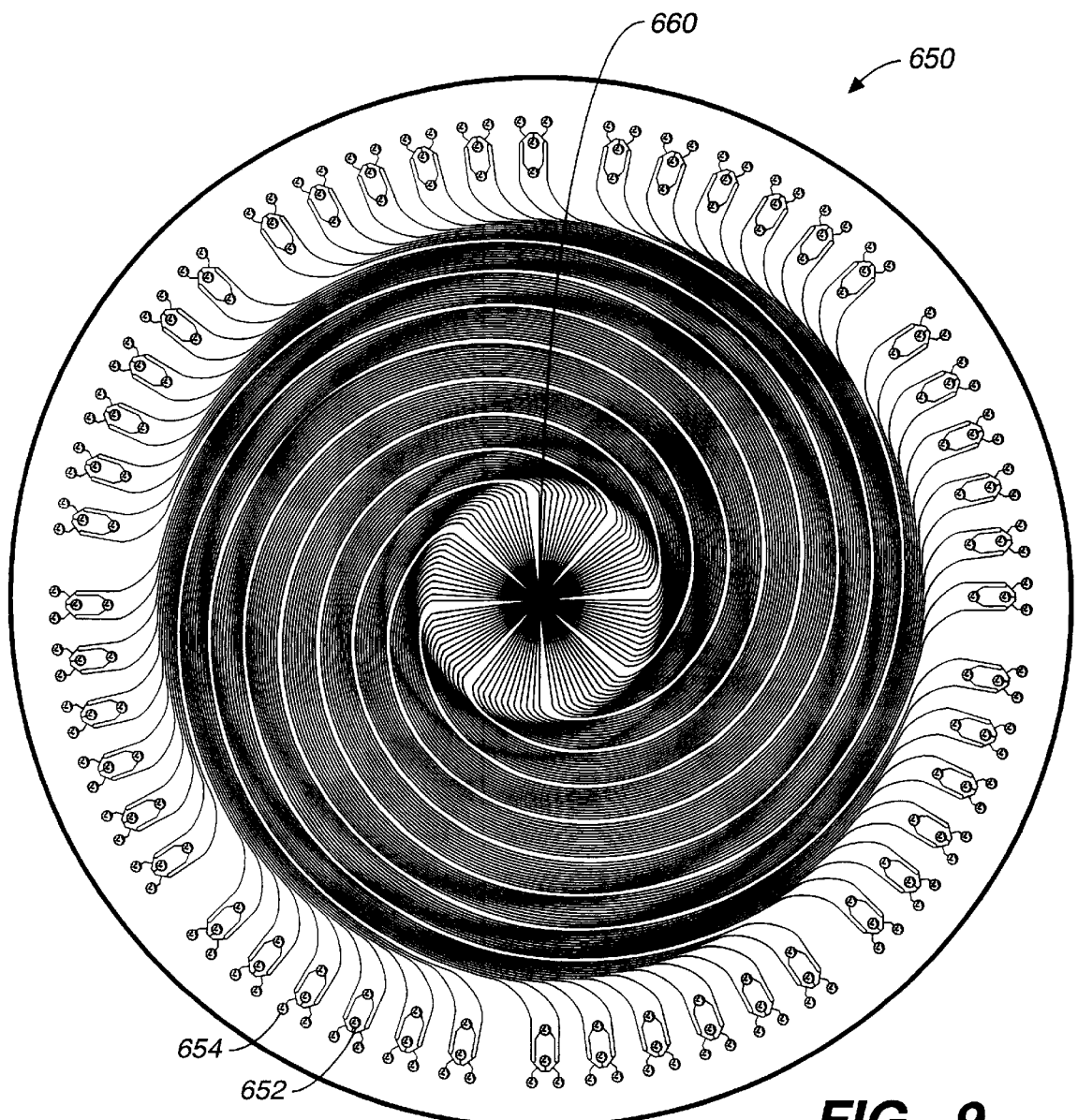
FIG._9

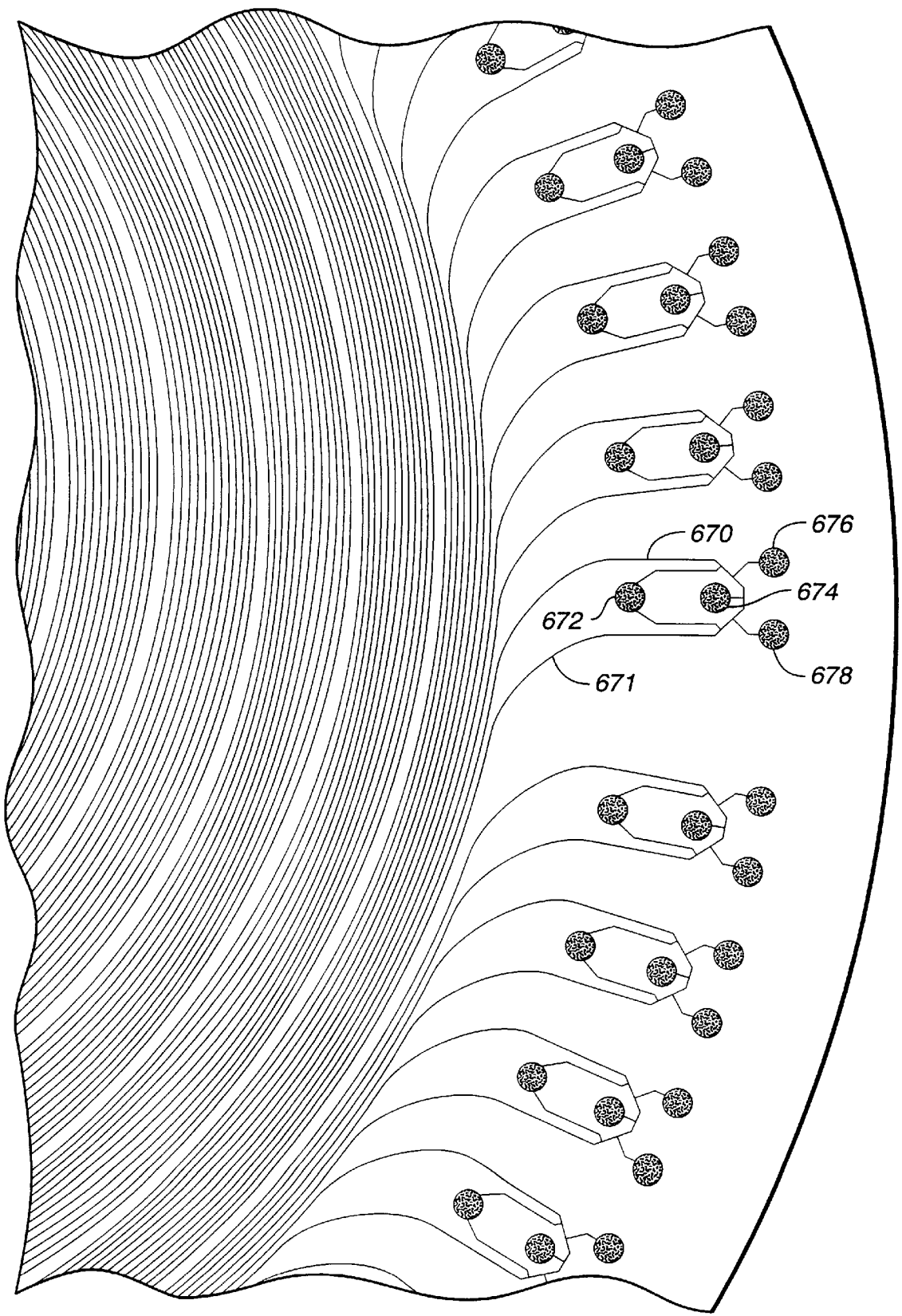
FIG._11

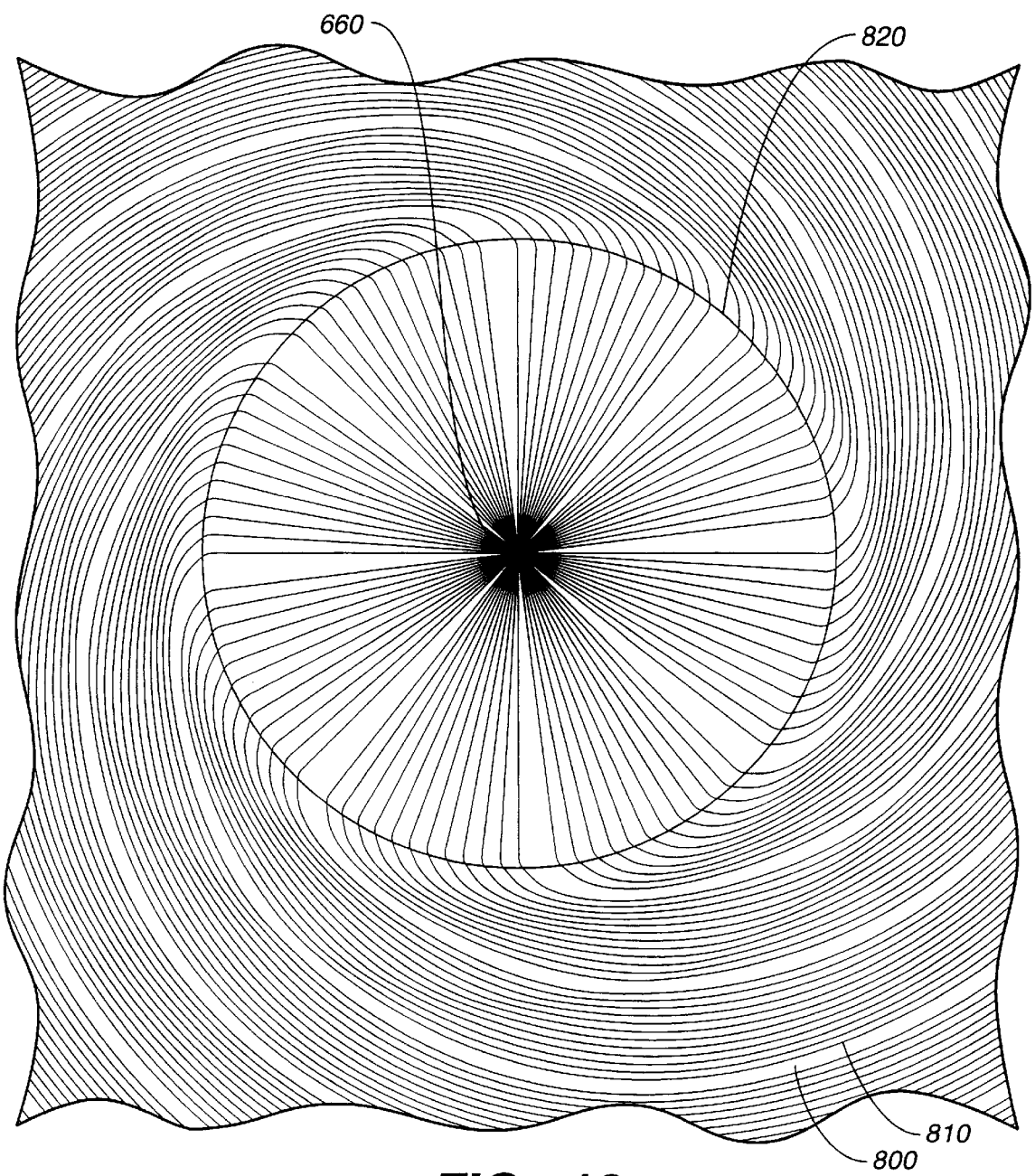
FIG._12

MICROFABRICATED CAPILLARY ARRAY ELECTROPHORESIS DEVICE AND METHOD

STATEMENT AS TO FEDERALLY SPONSORED RESEARCH

This invention was made with Government support under Grant No. DE-FG-91ER61125, awarded by the U.S. Department of Energy, and Grant No. HG01399, awarded by the National Institutes of Health. The Government has certain rights in the invention.

BACKGROUND OF THE INVENTION

This invention relates to electrophoresis generally, and more particularly, to an apparatus and method for performing capillary array electrophoresis on microfabricated structures.

In many diagnostic and gene identification procedures such as gene mapping, gene sequencing and disease diagnosis, deoxyribonucleic acid (DNA), ribonucleic acid (RNA) or proteins are separated according to their physical and chemical properties. In addition to DNA, RNA or proteins, other small molecule analytes may also need to be separated.

One electrochemical separation process is known as electrophoresis. In this process, molecules are transported in a capillary or a channel which is connected to a buffer-filled reservoir. An electric field in the range of kilovolts is applied across both ends of the channel to cause the molecules to migrate. Samples are typically introduced at a high potential end and, under the influence of the electric field, move toward a low potential end of the channel. After migrating through the channel, the separated samples are detected by a suitable detector.

Typically, electrophoretic separation of nucleic acids and proteins is carried out in a gel separation medium. Although slab gels have played a major role in electrophoresis, difficulties exist in preparing uniform gels over a large area, in maintaining reproducibility of the different gels, in loading sample wells, in uniformly cooling the gels, in using large amounts of media, buffers, and samples, and in requiring long run times for extended reading of nucleotides. Moreover, slab gels are not readily amenable to a high degree of multiplexing and automation. Recently, microfabricated capillary electrophoresis (CE) devices have been used to separate fluorescent dyes and fluorescently labeled amino acids. Additionally, DNA restriction fragments, polymerase chain reaction (PCR) products, short oligonucleotides and even DNA sequencing fragments have been effectively separated with CE devices. Also, integrated micro-devices have been developed that can perform polymerase chain reaction amplification immediately followed by amplicon sizing, DNA restriction/digestion and subsequent size-based separation, and cells sorting and membrane lysis of selected cells. However, these micro-fabricated devices only perform analysis on one channel at a time. For applications such as population screening or DNA sequencing, such a single channel observation and analysis results in an unacceptable delay for screening many members of a population.

SUMMARY OF THE INVENTION

The invention provides a capillary array electrophoresis (CAE) micro-plate. The micro-plate has an array of separation channels connected to an array of sample reservoirs on the plate. The sample reservoirs are organized into one or more sample injectors. A waste reservoir is provided to collect wastes from sample reservoirs in each of the sample injectors. Additionally, a cathode reservoir is multiplexed with one or more separation channels. An anode reservoir which is common to some or all separation channels is also provided on the micro-plate. Moreover, the distance from the anode to each of the cathodes is kept constant by deploying folded channels. The corners on these turns may be right angle turns or more preferably, smooth curves to improve electrophoretic resolution.

In one aspect, the reservoir layout on the substrate separates the sample reservoirs by a predetermined spacing to facilitate the simultaneous loading of multiple samples.

In another aspect, cathode, anode and injection waste reservoirs are combined to reduce the number of holes N in the substrate to about 5/4N where N is the number of samples analyzed.

In another aspect, the separation channels are formed from linear segments.

In another aspect, the separation channels are formed from curvilinear segments, which may include radial segments.

In yet another aspect, the separation channels span from the perimeter of the plate to the central region of the plate. The separation channels may span the plate in a linear or a radial fashion.

In yet another aspect, a CAE micro-plate assembly is formed using a micro-plate, a reservoir array layer, and an electrode array. The assembly simplifies sample handling, electrode introduction and allows an increased volume of buffer to be present in the cathode and anode reservoirs.

Advantages of the invention include the following. The micro-plate of the present invention permits analysis of a large number of samples to be performed at once on a small device. Moreover, the micro-plate allows samples to be easily loaded while minimizing the risk of contamination. Additionally, the micro-plate is easy to electrically address. Further, the micro-plate supports a wide variety of formats that can provide higher resolution separation and detection of samples, faster separation and detection of samples, or separation and detection of more samples.

Other features and advantages will be apparent from the following description and the claims.

BRIEF DESCRIPTION OF THE DRAWINGS

The accompanying drawings, which are incorporated in and constitute a part of the specification, schematically illustrate the present invention and, together with the general description given above and the detailed description given below, serve to explain the principles of the invention.

FIG. 1 is a capillary array electrophoresis (CAE) micro-plate layout.

FIG. 2 is a schematic illustration of the sample injector of FIG. 1.

FIGS. 3A–3D are illustrations of the operation of the sample injector of FIG. 2.

FIG. 4A is an exploded perspective view of a CAE micro-plate assembly.

FIG. 4B is a cross-sectional side view of the CAE micro-plate assembly of FIG. 4A.

FIG. 5 is an illustration of a laser excited galvo-scanner in conjunction with a CAE micro-plate.

FIGS. 6A and 6B are images of separations of genetic markers for hereditary hemochromatosis.

FIG. 7 is a plot of electropherograms generated from the images of FIGS. 6A and 6B.

FIG. 8 is a second CAE micro-plate layout.

FIG. 9 is a third CAE micro-plate layout.

FIG. 10 is a schematic illustration of a sample injector of FIG. 9.

FIG. 11 is an enlarged view of a perimeter portion of the CAE micro-plate layout of FIG. 9.

FIG. 12 is an enlarged view of a center portion of the CAE micro-plate layout of FIG. 9.

DESCRIPTION

Referring now to FIG. 1, a capillary array electrophoresis (CAE) micro-plate 10 is shown. The micro-plate 10 has an array of capillaries or separation channels 50 etched thereon. In one embodiment of FIG. 1, 48 individual separation channels are etched in a 150 micron ($\mu$m) periodic array. In this embodiment, the separation channels 50 branch out to an 8×12 array of sample reservoirs 101, each of which is spaced a predetermined distance apart to facilitate loading with an 8-tipped pipetter. In this case, each sample reservoir 101 is spaced in one dimension nine millimeters apart from another sample reservoir. The separation channels 50 extend by a first predetermined distance from an injection region to an anode reservoir 180 and by a second predetermined distance from an injector group 100 to a cathode reservoir 120. The first predetermined distance may be about 10 centimeters, while the second predetermined distance may be about 1.8 centimeters.

Each of the sample reservoirs 101 belongs to an injector group such as one of injector groups 100–116. Additionally, injector groups 100, 102 and 104 are connected to a cathode reservoir 120. Although the cathode reservoir 120 is connected to three sample injectors 100, 102 and 104, other cathode injectors may be connected to more than three sample injectors. For instance, a cathode injector 130 is connected to sample injectors 106, 108, 110, 112, 114 and 116.

The anode reservoir 180 is placed in a non-symmetrical manner in this case to avoid a conflict with a scanning system. Moreover, the distance for paths from the anode reservoir 180 to any one of cathodes 120 or 130 is identical for all separation channels. The equal distance is achieved by providing folded paths connecting certain sample reservoirs that are close to the anode 180 to increase the path length and to achieve a uniform distance between the anode reservoir 180 and the cathode reservoirs 120 and 130 for all sample reservoirs.

In the embodiment of FIG. 1, the number of holes H in the micro-plate 10 is about 5N/4, and more exactly, 5N/4+7, where N is a number of samples. As the embodiment of FIG. 1 addresses 96 samples in parallel, 127 holes are required to be drilled. This number of holes is close to a theoretical minimum number of holes of N+3. The reduction in hole counts is advantageous as fewer holes need to be drilled into the micro-plate 10, thereby increasing manufacturing efficiency as well as decreasing the potential for defects in the production of micro-plates, as caused by mechanical stress associated with the drilling process. Another reason for multiplexing the cathode, anode and waste reservoirs is to make it more feasible to fit 96 separation system on a single substrate. The above advantages are also applicable in the event that the holes are formed by a molding process or a bonding process in lieu of the drilling process.

Turning now to FIG. 2, details of the sample injector 100 of FIG. 1 are shown. The sample injector 100 has a plurality of sample reservoirs 200, 204, 220 and 224. Sample reservoirs 200 and 220 contain a first sample, while sample reservoirs 204 and 224 contain a second sample.

The sample injector 100 also has a first separation channel 202 and a second separation channel 222. The sample injector 100 thus permits a serial analysis of two different samples on each separation channel. The first and second separation channels 202 and 222 are connected to a waste reservoir 208 by a cross channel 207. The sample injector 100 also has a cathode end 210 as well as an anode end 212. The cathode and anode ends 210 and 212 are at opposite ends of the first separation channel 202. Similarly, a second cathode end 214 is connected to a second anode end 216 by a separation channel 222 that is connected to the waste reservoir 208. As illustrated below, by a proper biasing of the anode reservoirs 211 and 212, cathode reservoirs 200 and 214, sample reservoirs 200, 204, 220, 224, and waste reservoir 208, samples may be moved from their respective sample reservoirs 200, 204, 220 and 224 through the cross channel to the waste reservoir thereby facilitating an insertion into the separation channel.

Referring now to FIGS. 3A, 3B, 3C and 3D, a process for loading a sample from its respective sample reservoir into the cross channel and then performing a separation is shown. In FIG. 3A, an injection voltage, preferably about 300 volts (3.0 V/cm), is applied between the sample reservoir 200 and the injection waste reservoir 208 to draw a sample through a channel that passes from the sample reservoir to the waste reservoir and crosses the separation channel.

In FIG. 3B, a separation voltage of about 3700 volts (300 V/cm), for example, is applied between the cathode end 210 and the anode end 212. This causes the electrophoretic separation of the sample. In addition, a back-bias of the potential between the sample reservoir 200 and the injection waste reservoir 208 is applied. Preferably, the back biasing voltage is about 720 volts. The back-biasing operation clears excess samples from the injection cross-channel 213. As illustrated in FIG. 3B, a 100 $\mu$m sample plug is injected and any residual sample is pulled away from the injection region to avoid tailing side-effects.

FIGS. 3C and 3D represents analogous injections from the second sample reservoir 204. Although the embodiment of FIGS. 2 and 3A–3D operates on two samples, four samples may be injected onto a single capillary without any significant cross-contamination.

The process of etching patterns into a representative micro-plate is discussed next. In one microfabricated embodiment, Borofloat glass wafers available from Schott Corporation of Yonkers, N.Y. are pre-etched in 49% HF for 15 sec and cleaned before deposition of an amorphous silicon sacrificial layer of about 1500 Å in a plasma enhanced chemical vapor deposition (PECVD) system. The wafers are primed with hexamethyldisilazane, spin coated at 5000 rpm with a photoresist such as a 1818 photoresist available from Shipley Corp. of Marlborough, Mass. The photoresist is developed in a 1:1 mixture of Microposit developer concentrate available from Shipley and water. The wafers are then soft-baked at 90° C. for 30 minutes. The mask pattern is transferred to the substrate by exposing the photoresist to ultraviolet radiation in a Quintel contact mask aligner. The mask pattern is transferred to the amorphous silicon by a $CF_4$ plasma etch performed in the PECVD reactor. The wafers are etched in a 49% HF solution for about 3 minutes at an etch rate of 7 $\mu$m/min to form a final etch depth of 21 $\mu$m and channel width of ~60 $\mu$m at the bonded surface. The photoresist is stripped and the remaining amorphous silicon is removed in a $CF_4$ plasma etch. Holes are drilled into the etched plate using a 1.25 mm diameter diamond-tipped drill bit, available from Crystalite Corporation of Westerville, Ohio. The etched and drilled plate is thermally bonded to a flat wafer of similar size and type in a programmable vacuum furnace. After bonding, the channel surfaces are coated using a coating protocol.

Turning now to FIGS. 4A and 4B, an exploded view and a cross-sectional side view of a CAE micro plate are shown. In FIG. 4A, a CAE micro-plate 302 with etched separation channels 301 and a plurality of reservoirs 303 formed thereon is provided. A reservoir array layer 304 is mounted above the CAE micro-plate 302 to provide additional reservoir space above the reservoirs formed on the micro-plate 302. The presence of the reservoir array layer 304 increases the volume of buffers in the cathode and anode reservoirs and simplifies sample handling and electrode introduction. Preferably, the reservoir array layer 304 is a one millimeter thick elastomer sheet which makes a watertight seal when it is in contact with the glass micro-plate 302. The reservoir array layer 304 may be an elastomer such as Sylgard 184, available from Dow Corning of Midland, Mich.

The reservoir array layer 304 is placed onto the microplate 302 before the channels are filled with a separation medium. Preferably, the separation medium is 0.75 percent weight/volume hydroxyethylcellulose (HEC) in a 1× TBE buffer with 1 $\mu$M ethidium bromide. Additionally, the reservoir array 304 fully isolates the reservoirs from each other. The separation channels are pressure filled with a sieving matrix from the anode reservoir 180 until all channels have been filled. The anode and cathode reservoirs 180 and 120 are then filled with a 10× TBE buffer to reduce ion depletion during electrophoresis. The sample reservoirs are rinsed with deionized water. Samples are then loaded from a micro-titer plate using an 8-tipped pipetter.

After the reservoir array layer 304 is positioned on the micro-plate 302, an electrode array 306 is placed above the reservoir array 304. The electrode array 306 is fabricated by placing an array of conductors such as platinum wires through a printed circuit board. Each conductor is adapted to engage a reservoir on the micro-plate 302. Moreover, the wires are electrically connected with metal strips on the circuit board to allow individual reservoirs of a common type to be electrically addressed in parallel. The electrode array 306 also reduces the possibility of buffer evaporation. The electrode array 306 in turn is connected to one or more computer controlled power supplies.

As shown in FIG. 4B, the reservoir array layer 304, when used in conjunction with the micro-plate 302, enlarges the effective volume of the reservoirs originally formed on the micro-plate 302. Moreover, electrodes from the electrode array 306 are adapted to probe the reservoirs on the microplate 302 and the reservoir array layer 306. The solutions are placed in the reservoirs by a pipetter 308.

After assembly, the CAE micro-plate 302 is probed with a galvo-scanner system 400, as shown in FIG. 5. The system 400 measures fluorescence using a detector at a detection zone of the channels. During the process of electrophoresis, as a fluorescent species traverses a detection zone, it is excited by an incident laser beam. In a direct fluorescence detection system, either the target species is fluorescent, or it is transformed into a fluorescent species by tagging it with a fluorophore. The passing of the fluorescent species across the detection zone results in a change, typically an increase in fluorescence that is detectable by the system 400.

Turning now to the analysis system, the galvo-scanner 400 has a frequency-doubled YAG laser such as YAG laser available from Uniphase Corporation of San Jose, Calif. The YAG laser generates a beam which may be a 30 mW, 532 nm beam. The beam generated by the laser 402 travels through an excitation filter 404 and is redirected by a mirror 406. From the mirror 406, the beam travels through a beam expander 408. After expansion, the beam is directed to a dichroic beam splitter 410. The laser beam is directed to a galvonometer 420 which directs the beam to a final lens assembly 422. In this manner, the beam is focused on a spot of about 5 $\mu$m where it excited flourescence from the molecules in the channels and is scanned across the channels at 40 Hz. The resulting flourescence is gathered by the final lens and passed through the galvomirror and the dichroic beam splitter 410 to an emission filter 412 which operates in the range of about 545–620 nm. After passing through the emission filter 412, the beam is focused by a lens 414. Next, the beam is directed through a pinhole 416 such as a 400 $\mu$m pinhole for delivery to a photomultiplier (PMT) 418.

The electrode array 306 is connected to one or more power supplies 428 such as a series PS300, available from Stanford Research Systems of Sunnyvale, Calif. The power supplies are connected to a computer and software controlled to automatically time and switch the appropriate voltages into the electrode array 306. The software may be written in a conventional computer language, or may be specified in a data acquisition software such as LabVIEW, available from National Instruments of Austin, Tex. Data corresponding to spatially distinct fluorescent emission may then be acquired at about 77 kHz using a 16 bit A/D converter from Burr-Brown Corporation of Tucson, Ariz. Logarithmic data compression is then applied to generate five linear orders of dynamic measurement range. The data is obtained as a 16 bit image, and electropherograms are then generated using a suitable software such as IPLab, available from Signal Analytics, Vienna, Va., to sum data points across each channel. A detection of all lanes with a 0.09 second temporal resolution has been achieved by the system 400.

EXPERIMENTS

An electrophoretic separation and fluorescence detection of HFE, a marker gene for hereditary hemochromatosis, was performed to demonstrate the high-throughput analysis of biologically relevant samples using the CAE micro-plates of the present invention. HFE is a genetic disorder that causes a buildup of iron in tissues resulting over time in disease. The buildup primarily affects the liver. Between 0.1 and 0.5% of the Caucasian population are homozygous for an HFE C282Y variant responsible for this disease. If detected early, treatment can be initiated and long term effects avoided. To screen the population for this marker gene, a high throughput screening system is needed.

In this experiment, samples were prepared using PCR amplification and digestion to assay the C282Y mutation in the HFE gene. This G A mutation at nucleotide 845 creates a Rsa I restriction site in the HFE gene. DNA materials were isolated from peripheral blood leukocytes using standard methods. A segment of an HFE exon containing the variant site was amplified with the following primers:

HH-E4B: 5'GACCTCTTCAGTGACCACTC3'
HC282R: 5'CTCAGGCACTCCTCTCAACC3'

The HC282R primer is a primer discussed in Feder et al., Nature Genet. 13, 399–408 (1996), hereby incorporated by reference. The HH-E4B primer contains a 5' biotin tag. The 25 $\mu$l amplification reaction contained 10 mM Tris-HCl (pH=8.8), 50 mM KCl, 0.75 mM $MgCl_2$, 0.2 mM dNTPs, 7.5 pM of each primer and 1.5 U AmpliTaq DNA, available from Perkin Elmer, Branchburg, N.J. The PCR was carried out under three consecutive conditions: 5 cycles (95° C. for 1 min, 64° C. for 1 min, 72° C. for 1 min), 5 cycles (95° C. for 1 min, 60° C. for 1 min, 72° C. for 1 min), and 25 cycles (95° C. for 1 min, 56° C. for 1 min, 72° C. for 1 min). The restriction digestion of amplified product was carried out by adding 4 μl of each amplified sample to 6 μl buffer containing 2 U Rsa I (Sigma, St. Louis, Mo.) and digesting for 90 minutes at 37° C. Samples were dialyzed against DI water on a 96 sample dialysis plate, available from Millipore, Bedford, Mass. Sample types were initially established by separation of restriction fragments on 1% Agarose-3% Sea-Plaque gel, available from FMC Bioproducts, Rockland, Me, in 0.5×TBE. Gels were stained in 0.5 μg/ml ethidium bromide for 30 minutes and visualized on a UV transilluminator, a Spectroline model TR-302, using a 123-bp ladder, available from Life Technologies Inc., Gaithersburg, Md., to determine fragment sizes.

FIG. 6A and 6B present images of separations of 96 HFE samples on a CAE micro-plate. The 96 samples were separated in two runs of 48 samples, corresponding to two injection reservoirs per channel. In this experiment, nineteen different samples were dispersed among the 96 sample wells, giving a 5-fold redundancy in sample analysis. An original image 500 was obtained for the first injection, while an original image 504 was obtained for the second injection. Additionally, expanded images 502 and 506, corresponding to original images 500 and 504 are shown. The width of the electrophoretic image shown is 7.4 mm for 48 lanes and the complete analysis of 96 samples was performed in under 8 minutes. The expanded images show that the bands are of high intensity and resolution. The image exhibits a smile with the right lanes about 20 seconds faster than the left. This is caused by a gradient in the electrophoresis voltages caused by the placement of the anode to the side of the injection region to ensure adequate clearance from the scanning lens.

FIG. 7 presents the 96 electropherograms obtained from the images in FIGS. 6A and 6B. All electropherograms have been shifted to align a 167-bp doublet in order to compare the separations. The 167-bp fragment appears as a doublet due to a partial biotinylation of the HH-E4B primer, as the biotinylated form accounts for the slower migrating fragment in the doublet. The 167-bp doublet provides a useful reference point for the alignment of electropherograms to compare separations and allows an accurate genotyping without requiring a sizing ladder. As shown in FIG. 7, an average distance between the 111 and 140-bp bands is 7.3 seconds with a standard deviation (SD) of 0.8 second and 0.6 second, respectively, for the first injection and 6.6 sec with a SD of 1.1 second and 0.5 second, respectively, for the second injection. Using a t-test, the typings for both injections are determined to be at about a 99.9% confidence level.

Referring to FIG. 8, a second embodiment of the CAE micro-plate 600 is shown. In FIG. 8, the micro-plate 600 is an array of injectors, each of which includes waste reservoirs 602 and 608, sample reservoirs 604, 606, 610 and 612. Each injector unit is connected to one of two cathode reservoirs 614 or 616, respectively. Additionally, each injector unit is connected to one capillary in an array of capillaries or channels 620. The capillaries or channels 620 are connected to an anode 630. In this design, 96 samples can be analyzed by injecting four samples serially on a single capillary. Further, 24 separation capillaries or channels are used to analyze the material in 96 sample reservoirs. Moreover, each of the injector units has two waste reservoirs. In total, the embodiment of FIG. 8 has a hole count of 3N/2+3.

Referring now to FIG. 9, a third embodiment of the CAE micro-plate 650 is disclosed. In the CAE micro-plate 650 of FIG. 9, cathode reservoirs 652 are positioned on a perimeter of the CAE micro-plate 650. Additionally, an anode reservoir 660 is positioned in the center of the CAE micro-plate 650. Separation channels or capillaries may emanate from an outer perimeter of the micro-plate 650 toward the center of the micro-plate 650 in a spiral pattern if longer separation channels are desired. Alternatively, if short paths are desired, the separation channels or capillaries may simply be a straight line connecting the perimeter of the micro-plate 650 to the center 660 of the CAE micro-plate 650.

Turning now to FIGS. 10 and 11, an injector unit of the CAE micro-plate of FIG. 9 and its position on a perimeter of the micro-plate of FIG. 9 are illustrated in detail. In FIG. 10, two separation channels or capillaries 670 and 671 are connected to a common waste reservoir 672 and a common cathode reservoir 674. Additionally, the separation channels 670 and 671 are connected to sample reservoirs 676 and 678. As shown in FIGS. 10 and 11, the connections between the sample and waste reservoirs may intersect in an off-set manner.

Referring now to FIG. 12, the common anode 660 of FIG. 9 is illustrated in detail. As shown in FIG. 11, a plurality of separation channels or capillaries 800–810 form a curvilinear pattern, which may be a radial pattern, converging on a central region 820. From the central region 820, the separation channels or capillaries form a passageway from the perimeter of the central region 820 to the common anode reservoir 660 at the center of the CAE micro-plate. The center area 820 is the area where a rotating scanner may be used for detection purposes.

Samples may be loaded manually or automatically. Serial injections may be used to increase the sample throughput with a predetermined number of capillaries. Moreover, while one embodiment of the present invention injects two samples per channel, an injection of four samples per channel may be used to analyze 192 samples per plate. Further, an increase in the number of capillaries on the CAE micro-plate would increase the throughput correspondingly without introducing any sample contamination. Moreover, the plate may be made of glass or plastic.

In addition, the scanning detection system may be altered by inverting its objective lens and scanning from below. Placing of the optics below the plate would permit facile manipulation and introduction of samples. The inverted scanning would also avoid spatial conflict with the anode reservoir, thereby permitting a central placement of the anode. Moreover, an array of PCR reaction chambers may be used with the micro-plate of the invention to allow for integrated amplification of low volume samples, eliminate sample handling and manual transfer, and reduce cost. Furthermore, the present invention contemplates that electronic heaters, thermocouples and detection systems may be used with an array of microfluidic capillaries to enhance the CAE electrophoresis process.

While the invention has been shown and described with reference to an embodiment thereof, those skilled in the art will understand that the above and other changes in form and detail may be made without departing from the spirit and scope of the following claims.

What is claimed is:

1. A capillary array electrophoresis plate, comprising:
   one or more anode reservoirs;
   a plurality of separation channels connected to said anode reservoirs; and
   one or more injectors formed in said plate, each injector including:

two or more sample reservoirs coupled to said separation channels;

a plurality of waste reservoirs connected to said separation channels; and at least one cathode reservoir multiplexed with two or more of said separation channels.

2. The plate of claim 1, further comprising an electrode array coupleable to said reservoirs.

3. The plate of claim 1, wherein the plate has an outer perimeter and a center and the separation channels connect the outer perimeter to the center.

4. A capillary array electrophoresis plate comprising:

an array of microfabricated separation channels formed at a surface of a first microfabricated substrate and a corresponding surface of a second substrate bonded to the surface of said first substrate, each of said channels including a first end and a second end;

an array of sample reservoirs connected to said array of separation channels;

an array of waste reservoirs connected to said array of separation channels;

an array of cathode reservoirs connected to the first end of each of the separation channels;

an array of anode reservoirs, wherein at least one anode reservoir is connected to the respective second ends of at least two of the separation channels; and an injector formed by an injection channel connected to a sample reservoir that crosses a separation channel and connects to a waste reservoir.

5. A capillary array electrophoresis plate comprising:

an array of microfabricated separation channels formed on a surface of a first microfabricated substrate and a corresponding surface of a second substrate bonded to the surface of said first substrate, each of said channels having a first end and a second end;

an array of sample reservoirs connected to said array of separation channels;

an array of waste reservoirs connected to said array of separation channels;

an array of anode reservoirs connected to the second end of each of the separation channels;

an array of cathode reservoirs, wherein at least one cathode reservoir is connected to the respective first ends of at least two of the separation channels; and an injector formed by an injection channel crossing one of said separation channels, said injection channel connecting one sample reservoir of said array of sample reservoirs to one waste reservoir of said array of waste reservoirs.

6. A capillary array electrophoresis plate comprising:

an array of microfabricated separation channels formed on a surface of a first microfabricated substrate and a corresponding surface of a second substrate bonded to the surface of said first substrate, each of said channels having a first end and a second end;

an array of sample reservoirs connected to said array of separation channels wherein each separation channel of the array of separation channels is in fluid communication with at least one dedicated sample reservoir; and an array of waste reservoirs connected to said separation channels, wherein at least one waste reservoir is multiplexed to two or more of said channels.

7. The capillary array electrophoresis plate of claim 4, 5, or 6, wherein both substrates are made of glass.

8. The capillary array electrophoresis plate of claim 4, 5, or 6, wherein both substrates are made of plastic.

9. The capillary array electrophoresis plate of claim 4 or 5, further comprising a reservoir array layer mounted above the plate, the reservoir array layer including openings positioned to couple to a combination of the sample reservoirs, the waste reservoirs, the cathode reservoirs, and the anode reservoirs.

10. The plate of claim 9, further comprising an electrode array coupleable to said reservoir array layer.

11. The capillary array electrophoresis plate of claim 10 wherein said electrode array is integral with the two substrates.

12. The capillary array electrophoresis plate of claim 11, wherein the sample reservoirs are regularly spaced on the plate to receive solutions from a parallel loading device.

13. The capillary array electrophoresis plate of claim 4 or 5, wherein the first substrate includes an array of electrodes aligned with the sample reservoirs, the waste reservoirs, the cathode reservoirs, and the anode reservoirs to make electrical contacts with a plurality of solutions in a combination of the sample reservoirs, the waste reservoirs, the cathode reservoirs, and the anode reservoirs.

14. The capillary array electrophoresis plate of claim 4, or 5, wherein the capillary array electrophoresis plate has H holes, and wherein H is approximately equal to 5N/4, with N being the number of samples to be processed.

15. The capillary array electrophoresis plate of claim 4, 5, or 6, wherein the capillary array electrophoresis plate is made of a combination of glass and plastic.

16. The capillary array electrophoresis plate of claim 4, 5, or 6, further comprising an electrode array in electrical contact with the plate.

17. The capillary array electrophoresis plate of claim 4 or 5, wherein at least one waste reservoir of said array of waste reservoirs is multiplexed with two or more of said separation channels.

18. The capillary array electrophoresis plate of claim 6, further comprising a reservoir array layer mounted above the plate, the reservoir array layer including openings positioned to connect to a combination of the sample reservoirs and the waste reservoirs.

19. The capillary array electrophoresis plate of claim 6, wherein the first substrate includes an array of electrodes aligned with the sample reservoirs and the waste reservoirs to make electrical contacts with a plurality of solutions in a combination of the sample reservoirs and the waste reservoirs.

20. A capillary array electrophoresis plate, comprising:

a plurality of separation channels formed in said plate;

a plurality of sample reservoirs connected to said separation channels wherein each separation channel of the plurality of separation channels is in fluid communication with at least one dedicated sample reservoir; and an anode reservoir multiplexed to two or more of the plurality of separation channels.

21. A capillary electrophoresis plate, comprising:

a plurality of separation channels formed in said plate;

a plurality of sample reservoirs coupled to said separation channels wherein each separation channel of the plurality of separation channels is in fluid communication with at least one dedicated sample reservoir; and a cathode reservoir multiplexed to two or more of the plurality of separation channels.

22. A capillary array electrophoresis plate, comprising:

a plurality of separation channels formed in said plate;

a plurality of sample reservoirs coupled to said separation channels wherein each separation channel of the plurality of separation channels is in fluid communication with at least one dedicated sample reservoir; and a waste reservoir multiplexed to two or more of the plurality of separation channels.

23. The plate of claim 20, 21, or 22, further comprising a reservoir array layer mounted on the plate.

24. The plate of claim 23, further comprising an array of electrodes insertable into and positioned above said reservoir array layer.

25. The plate of claim 20, 21, or 22, wherein said plurality of sample reservoirs are regularly spaced in said plate and adapted to engage a parallel loading device.

26. The capillary array electrophoresis plate of claim 25, wherein the parallel loading device comprises a multi-headed pipetter.

27. The capillary array electrophoresis plate of claim 20, 21, or 22, further comprising an electrode array in electrical contact with said plate.

28. The capillary array electrophoresis plate of claims 1, 4, 20, 21, 22, 5 or 6, wherein, the separation channels are disposed in a radial pattern on the capillary array electrophoresis plate.

29. A method for injecting a sample through a capillary array electrophoresis plate, comprising:

connecting a cathode reservoir to respective first ends of two or more separation channels;

connecting an anode reservoir to respective second ends of two or more of said separation channels;

connecting a sample reservoir and a waste reservoir together by a cross channel that crosses one of said separation channels;

applying an injection voltage between the sample reservoir and the waste reservoir to draw the sample into the cross channel while applying a bias voltage to the cathode reservoir and the anode reservoir to control an injection plug width;

applying a running voltage between the cathode and anode reservoirs; and applying a biasing voltage to the waste reservoir and the sample reservoir to pull away residuals of the sample.

30. A method of forming a capillary array electrophoresis plate, comprising:

forming a plurality of separation channels in said plate;

forming a plurality of sample reservoirs connected to said separation channels wherein each separation channel of the plurality of separation channels is in fluid communication with at least one dedicated sample reservoir; and connecting an anode reservoir to two or more of the plurality of separation channels.

31. A method of forming a capillary array electrophoresis plate, comprising:

forming a plurality of separation channels in said plate;

forming a plurality of sample reservoirs connected to said separation channels wherein each separation channel of the plurality of separation channels is in fluid communication with at least one dedicated sample reservoir; and connecting a cathode reservoir to two or more of the plurality of separation channels.

32. A method of forming a capillary array electrophoresis plate, comprising:

forming a plurality of separation channels in said plate;

forming a plurality of sample reservoirs connected to said separation channels wherein each separation channel of the plurality of separation channels is in fluid communication with at least one dedicated sample reservoir; and connecting a waste reservoir to two or more of the plurality of sample reservoirs.

33. The method of claims 29, 30, 31 or 32, wherein, the separation channels are disposed in a radial pattern on the capillary array electrophoresis plate.

34. A method of forming a capillary array electrophoresis plate, comprising:

forming an array of microfabricated separation channels;

forming an array of sample reservoirs;

connecting the array of sample reservoirs to the array of microfabricated separation channels;

connecting one or more cathode reservoirs to said array of separation channels, wherein at least one cathode reservoir is connected to two or more separation channels of said array of separation channels;

connecting one or more anode reservoirs to said array of separation channels, wherein at least one anode reservoir is connected to two or more separation channels of said array of separation channels; and connecting an array of waste reservoirs to said array of separation channels, wherein at least one waste reservoir of said array of waste reservoirs is connected to two or more sample reservoirs of said array of sample reservoirs.

35. The method of claim 34, wherein a distance from each cathode reservoir to a point where a sample reservoir of said array of sample reservoirs is connected to said channel is approximately equal for each separation channel.

36. The method of claim 34, wherein a distance from each anode reservoir to a point where a sample reservoir of said array of sample reservoirs is connected to said channel is approximately equal for each separation channel.

37. A capillary array electrophoresis plate, comprising:

a first set of cathode reservoirs positioned near an outer perimeter of the plate;

a second set of anode reservoirs positioned near a center of the plate, wherein the number of reservoirs in said second set is fewer than the number of reservoirs in said first set; and an array of separation channels connecting the first set of reservoirs to the second set of reservoirs.

38. The capillary array electrophoresis plate of claim 37, wherein said array of separation channels radially connect said first set of reservoirs to said second set of reservoirs.

39. A capillary array electrophoresis plate, comprising:

a separation channel formed in said plate connected to a cathode reservoir and an anode reservoir;

a first cross channel connected to the separation channel at a first location, wherein a first end of the first cross channel connects to a first waste reservoir and a second end connects to a first sample reservoir; and a second cross channel connected to the separation channel at a second location; wherein a first end of the second cross channel connects to the first waste reservoir and a second end connects to a second sample reservoir.

40. A capillary array electrophoresis plate comprising:

an array of microfabricated separation channels formed on a surface of a first microfabricated substrate and a corresponding surface of a second substrate bonded to the surface of said first substrate, each of said channels having a first end and a second end;

an array of sample reservoirs connected to said array of separation channels wherein each of a plurality of individual separation channels are each in fluid communication with at least one dedicated sample reservoir; and an array of waste reservoirs connected to said separation channels, wherein at least one waste reservoir is multiplexed to two or more of said channels, wherein the capillary array electrophoresis plate has H holes, and wherein H is approximately equal to 5N/4, with N being the number of samples to be processed.

41. A capillary array electrophoresis plate comprising:

a microfabricated separation channel formed on a surface of a first microfabricated substrate and a corresponding surface of a second substrate bonded to the surface of said first substrate, said channel being connected to a cathode reservoir on one end and an anode reservoir on the other end; and two or more sample reservoirs sharing a waste reservoir and connected to the separation channel, wherein the capillary array electrophoresis plate has H holes, and wherein H is approximately equal to 5N/4, with N being the number of samples to be processed.

\* \* \* \* \*